US011028029B2

(12) United States Patent
Collier et al.

(10) Patent No.: US 11,028,029 B2
(45) Date of Patent: Jun. 8, 2021

(54) PROCESS FOR THE PRODUCTION OF 2,3,3,3-TETRAFLUOROPROPENE

(71) Applicant: Arkema France, Colombes (FR)

(72) Inventors: Bertrand Collier, Montbard (FR); Dominique Deur-Bert, Charly (FR); Anne Pigamo, Francheville (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/758,097

(22) PCT Filed: Nov. 8, 2018

(86) PCT No.: PCT/FR2018/052777
§ 371 (c)(1),
(2) Date: Apr. 22, 2020

(87) PCT Pub. No.: WO2019/092376
PCT Pub. Date: May 16, 2019

(65) Prior Publication Data
US 2020/0331826 A1 Oct. 22, 2020

(30) Foreign Application Priority Data
Nov. 13, 2017 (FR) ...................................... 1760635

(51) Int. Cl.
C07C 17/25 (2006.01)
B01J 23/26 (2006.01)
C07C 17/20 (2006.01)
C07C 21/18 (2006.01)

(52) U.S. Cl.
CPC ................ C07C 17/25 (2013.01); B01J 23/26 (2013.01); C07C 17/206 (2013.01); C07C 21/18 (2013.01)

(58) Field of Classification Search
CPC ......... C07C 17/21; C07C 19/08; C07C 17/25; C07C 17/206; Y02P 20/582; B01J 23/26
See application file for complete search history.

(56) References Cited

U.S. PATENT DOCUMENTS

| 2009/0240090 | A1 | 9/2009 | Merkel et al. | |
| 2012/0330073 | A1* | 12/2012 | Karube | C07C 17/21 570/156 |
| 2015/0203421 | A1 | 7/2015 | Takahashi et al. | |
| 2016/0251282 | A1 | 9/2016 | Bonnet et al. | |
| 2016/0297730 | A1* | 10/2016 | Chaki | C07C 17/087 |

FOREIGN PATENT DOCUMENTS

FR 3012137 A1 4/2015
WO 2013088195 A1 6/2013

OTHER PUBLICATIONS

ISA/EP; International Search Report and Written Opinion for International Patent Application No. PCT/FR2018/052777 dated Jul. 29, 2019, 12 pages.

* cited by examiner

Primary Examiner — Jafar F Parsa
(74) Attorney, Agent, or Firm — NK Patent Law

(57) ABSTRACT

The present invention relates to a process for the production of 2,3,3,3-tetrafluoropropene comprising the stages: i) in a first reactor, bringing 2-chloro-3,3,3-trifluoropropene into contact with hydrofluoric acid in the gas phase in the presence of a catalyst, in order to produce a stream A comprising 2,3,3,3-tetrafluoropropene, HF and unreacted 2-chloro-3,3,3-trifluoropropene; and ii) in a second reactor, bringing hydrofluoric acid into contact, in the gas phase in the presence or absence of a catalyst, with at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene, in order to produce a stream B comprising 2-chloro-3,3,3-trifluoropropene, characterized in that the stream A obtained in stage i) feeds said second reactor used for stage ii); and in that the pressure at the inlet of said first reactor of stage i) is greater than the pressure at the inlet of said second reactor of stage ii).

11 Claims, No Drawings

PROCESS FOR THE PRODUCTION OF 2,3,3,3-TETRAFLUOROPROPENE

CROSS-REFERENCE TO RELATED APPLICATIONS

This application is a U.S. National Stage application of International Patent Application No. PCT/FR2018/052777, filed on Nov. 8, 2018, which claims the benefit of French Patent Application No. 1760635, filed on Nov. 13, 2017.

TECHNICAL FIELD OF THE INVENTION

The present invention relates to the production of hydrofluoroolefins. More particularly, the present invention relates to the production of 2,3,3,3-tetrafluoropropene.

TECHNOLOGICAL BACKGROUND OF THE INVENTION

Halogenated hydrocarbons, in particular fluorinated hydrocarbons, such as hydrofluoroolefins, are compounds which have a structure of use as functional materials, solvents, refrigerants, inflation agents and monomers for functional polymers or starting materials for such monomers. Hydrofluoroolefins, such as 2,3,3,3-tetrafluoropropene (HFO-1234yf), are attracting attention because they offer a promising behavior as refrigerants having a low global warming potential.

Processes for the production of fluoroolefins are usually carried out in the presence of a starting substance, such as a chlorine-containing alkane or a chlorine-containing alkene, and in the presence of a fluorinating agent, such as hydrogen fluoride. These processes can be carried out in the gas phase or in the liquid phase, in the absence or not of a catalyst. For example, US 2009/0240090 discloses a gas-phase process for the preparation of 2-chloro-3,3,3-trifluoropropene (HCFO-1233xf) from 1,1,1,2,3-pentachloropropane (HCC-240db). The HCFO-1233xf thus produced is converted into 2-chloro-1,1,1,2-tetrafluoropropane (HCFC-244bb) in the liquid phase and then the latter is converted into 2,3,3,3-tetrafluoropropene.

WO 2013/088195 also discloses a process for the preparation of 2,3,3,3-tetrafluoropropene from 1,1,1,2,3-pentachloropropane and/or 1,1,2,2,3-pentachloropropane, comprising the stages: (a) catalytic reaction of 1,1,1,2,3-pentachloropropane and/or 1,1,2,2,3-pentachloropropane with HF to give a reaction mixture comprising HCl, 2-chloro-3,3,3-trifluoropropene, 2,3,3,3-tetrafluoropropene, unreacted HF and possibly 1,1,1,2,2-pentafluoropropane; (b) separating the reaction mixture into a first stream comprising HCl and 2,3,3,3-tetrafluoropropene and a second stream comprising HF, 2-chloro-3,3,3-trifluoropropene and possibly 1,1,1,2,2-pentafluoropropane; (c) catalytic reaction of said second stream to give a reaction mixture comprising 2,3,3,3-tetrafluoropropene, HCl, unreacted 2-chloro-3,3,3-trifluoropropene, unreacted HF and possibly 1,1,1,2,2-pentafluoropropane; and (d) supplying the reaction mixture obtained in stage c) directly to stage a) without separation.

There is still a need for more effective processes for the production of 2,3,3,3-tetrafluoropropene.

SUMMARY OF THE INVENTION

The present invention relates to a process for the production of 2,3,3,3-tetrafluoropropene comprising the stages:

i) in a first reactor, bringing 2-chloro-3,3,3-trifluoropropene into contact with hydrofluoric acid in the gas phase in the presence of a catalyst, in order to produce a stream A comprising 2,3,3,3-tetrafluoropropene, HF and unreacted 2-chloro-3,3,3-trifluoropropene; and ii) in a second reactor, bringing hydrofluoric acid into contact, in the gas phase in the presence or absence of a catalyst, with at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene, in order to produce a stream B comprising 2-chloro-3,3,3-trifluoropropene, characterized in that the stream A obtained in stage i) feeds said second reactor used for stage ii); and in that the pressure at the inlet of said first reactor of stage i) is greater than the pressure at the inlet of said second reactor of stage ii).

The present process makes it possible to optimize and improve the production of 2,3,3,3-tetrafluoropropene. Thus, the formation of heavy impurities can be minimized in the reaction loop. The decrease in the amounts of heavy impurities makes it possible to reduce the side reactions in order to ultimately facilitate the purification of the 2,3,3,3-tetrafluoropropene. The implementation of stage ii) at a lower pressure than in stage i) makes it possible in particular to decrease the formation of 1,1,1,2,2-pentafluoropropane. The content of 1,2-dichloro-3,3,3-trifluoropropene (HCFO-1223xd) is also decreased under these conditions.

According to a preferred embodiment, the pressure difference between the pressure at the inlet of said first reactor and the pressure at the inlet of said second reactor is from 100 mbar to 3.5 bar, advantageously from 150 mbar to 3.0 bar, preferably from 300 mbar to 2.5 bar, more preferentially from 400 mbar to 2.0 bar, in particular from 750 mbar to 1.75 bar, more particularly from 1 to 1.5 bar. The control of the pressure difference between the inlets of the two reactors in the abovementioned range makes it possible to optimize the subsequent conditions for purification of the 2,3,3,3-tetrafluoropropene. For example, a pressure difference as mentioned above makes it possible to easily control the operating conditions which can be used to purify the stream B as described in detail below in the present patent application. Thus, maintaining a pressure difference as mentioned above between the reactors used in stage i) and ii) makes it possible to keep a low content of impurities in the reaction loop while retaining an economically viable process.

According to a preferred embodiment, stage i) and stage ii) are carried out in the presence of a catalyst, preferably a chromium-based catalyst; in particular, said catalyst comprises a chromium oxyfluoride or a chromium oxide or a chromium fluoride or a mixture of these.

According to a preferred embodiment, the catalyst is based on chromium and also comprises a cocatalyst selected from the group consisting of Ni, Zn, Co, Mn and Mg; preferably, the content of cocatalyst is of between 0.01% and 10%, based on the total weight of the catalyst.

According to a preferred embodiment, the stream B also comprises 2,3,3,3-tetrafluoropropene, HF, HCl and 1,1,1,2,2-pentafluoropropane.

According to a preferred embodiment, the stream B is purified, preferably by distillation, in order to form a first stream comprising 2,3,3,3-tetrafluoropropene, HCl and 1,1,1,2,2-pentafluoropropane and a second stream comprising HF and 2-chloro-3,3,3-trifluoropropene.

According to a preferred embodiment, said second stream is recycled in stage i).

According to a preferred embodiment, said stream A and said at least one chlorinated compound are brought into contact prior to the entry of these into said second reactor.

According to one embodiment, the temperature at which stage i) is carried out is different from that at which stage ii) is carried out; and the difference between the temperature at which stage i) is carried out and the temperature at which stage ii) is carried out is greater than 0.2° C., advantageously greater than 0.5° C., preferably greater than 1° C., more preferentially greater than 5° C., in particular greater than 10° C.; and less than 60° C., advantageously less than 55° C., preferably less than 50° C., more preferentially less than 45° C., in particular less than 40° C., more particularly less than 35° C., favorably less than 30° C., preferentially favorably less than 25° C., particularly favorably less than 20° C. The difference between the temperature at which stage i) is carried out and the temperature at which stage ii) is carried out is expressed in absolute value.

According to a preferred embodiment, the stream B is cooled to a temperature of less than 100° C., then distilled in order to form said first stream comprising 2,3,3,3-tetrafluoropropene, HCl and 1,1,1,2,2-pentafluoropropane, and said second stream comprising HF and 2-chloro-3,3,3-trifluoropropene and possibly 1,2-dichloro-3,3,3-trifluoropropene; the temperature at the distillation column top is from −30° C. to 10° C. and the distillation is carried out at a pressure from 2 to 6 bara; said second stream obtained at the distillation column bottom is recycled in stage i).

DETAILED DESCRIPTION OF THE INVENTION

The present invention relates to a process for the production of 2,3,3,3-tetrafluoropropene comprising the stages:
  i) in a first reactor, bringing 2-chloro-3,3,3-trifluoropropene into contact with hydrofluoric acid in the gas phase in the presence of a catalyst, in order to produce a stream A comprising 2,3,3,3-tetrafluoropropene, HF and unreacted 2-chloro-3,3,3-trifluoropropene; and
  ii) in a second reactor, bringing hydrofluoric acid into contact, in the gas phase in the presence or absence of a catalyst, with at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene, in order to produce a stream B comprising 2-chloro-3,3,3-trifluoropropene.

Preferably, the stream A obtained in stage i) feeds said second reactor used for stage ii).

Preferably, the stream A can also comprise 1,1,1,2,2-pentafluoropropane.

According to a preferred embodiment, the stream B also comprises 2,3,3,3-tetrafluoropropene, HF, HCl and 1,1,1,2,2-pentafluoropropane. The stream B can also comprise 1,2-dichloro-3,3,3-trifluoropropene (HCFO-1223xd).

According to a preferred embodiment of the invention, the pressure at the inlet of said first reactor of stage i) is greater than the pressure at the inlet of said second reactor of stage ii).

Preferably, the pressure difference between the pressure at the inlet of said first reactor and the pressure at the inlet of said second reactor is from 100 mbar to 3.5 bar, advantageously from 150 mbar to 3.0 bar, preferably from 300 mbar to 2.5 bar, more preferentially from 400 mbar to 2.0 bar, in particular from 750 mbar to 1.75 bar, more particularly from 1 to 1.5 bar.

The process according to the invention is thus carried out under effective conditions making it possible to minimize the content of 1,2-dichloro-3,3,3-trifluoropropene (HCFO-1223xd) and/or 1,1,1,2,2-pentafluoropropane (HFC-245cb) in the stream B. Thus, the stream B can also comprise a content of 1,2-dichloro-3,3,3-trifluoropropene (HCFO-1223xd) of less than 10% by weight, based on the total weight of the organic compounds contained in said stream B, advantageously less than 8% by weight, preferably less than 7% by weight, more preferentially less than 6% by weight, in particular less than or equal to 5% by weight, based on the total weight of the organic compounds contained in said stream B. In addition, the stream B can also comprise a content of 1,1,1,2,2-pentafluoropropane (HFC-245cb) of less than 40% by weight, based on the total weight of the organic compounds contained in said stream B, advantageously less than 35% by weight, preferably less than 30% by weight, more preferentially less than 25% by weight, in particular less than or equal to 20% by weight, based on the total weight of the organic compounds contained in said stream B. The total weight of said stream B does not include the weights of HF and HCl also present in the stream B as mentioned above.

According to a preferred embodiment, stage i) and stage ii) are carried out in the presence of a catalyst, preferably a chromium-based catalyst. Preferably, the chromium-based catalyst can be a chromium oxide (for example $CrO_2$, $CrO_3$ or $Cr_2O_3$), a chromium oxyfluoride or a chromium fluoride (for example $CrF_3$) or a mixture of these. The chromium oxyfluoride can contain a fluorine content of between 1% and 60% by weight, based on the total weight of the chromium oxyfluoride, advantageously between 5% and 55% by weight, preferably between 10% and 52% by weight, more preferentially between 15% and 52% by weight, in particular between 20% and 50% by weight, more particularly between 25% and 45% by weight, favorably between 30% and 45% by weight, more favorably from 35% to 45% by weight, of fluorine, based on the total weight of the chromium oxyfluoride. The catalyst can also comprise a cocatalyst chosen from the group consisting of Ni, Co, Zn, Mg, Mn, Fe, Zn, Ti, V, Zr, Mo, Ge, Sn, Pb and Sb; preferably Ni, Co, Zn, Mg and Mn; in particular Ni, Co and Zn. The content by weight of the cocatalyst is of between 1% and 10% by weight, based on the total weight of the catalyst. The catalyst can be supported or not. A support, such as alumina, for example in its a form, activated alumina, aluminum halides ($AlF_3$, for example), aluminum oxyhalides, activated carbon, magnesium fluoride or graphite, can be used.

Preferably, the catalyst can have a specific surface between 1 and 100 m$^2$/g, preferably between 5 and 80 m$^2$/g, more preferentially between 5 and 70 m$^2$/g, ideally between 5 and 50 m$^2$/g, in particular between 10 and 50 m$^2$/g, more particularly between 15 and 45 m$^2$/g.

According to a preferred embodiment, the pressure at the inlet of said first reactor is atmospheric pressure or a pressure greater than this; advantageously, the pressure at the inlet of said first reactor is greater than 1.5 bara, preferably greater than 2.0 bara, in particular greater than 2.5 bara, more particularly greater than 3.0 bara. Preferably, stage i) is carried out at a pressure at the inlet of said first reactor of between atmospheric pressure and 20 bara, preferably between 2 and 18 bara, more preferentially between 3 and 15 bara.

Preferably, stage i) of the present process is carried out with a contact time between 1 and 100 s, preferably between 2 and 75 s, in particular between 3 and 50 s. Preferably, the HF/1233xf molar ratio can vary between 1:1 and 150:1, preferably between 2:1 and 125:1, more preferentially between 3:1 and 100:1. An oxidant, such as oxygen or chlorine, can be added during stage i). The molar ratio of the oxidant to the hydrocarbon compound can be between 0.005 and 2, preferably between 0.01 and 1.5. The oxidant can be pure oxygen, air or a mixture of oxygen and nitrogen.

As mentioned above, the pressure at the inlet of said second reactor is less than that at the inlet of said first reactor. Thus, the pressure at the inlet of said second reactor can be less than atmospheric pressure. The pressure at the inlet of said second reactor can be greater than 1.5 bara while being less than that at the inlet of said first reactor, preferably greater than 2.0 bara while being less than that at the inlet of said first reactor, in particular greater than 2.5 bara while being less than that at the inlet of said first reactor, more particularly greater than 3.0 bara while being less than that at the inlet of said first reactor. Preferably, stage ii) is carried out at a pressure of between atmospheric pressure and 20 bara while being less than that at the inlet of said first reactor, preferably between 2 and 18 bara while being less than that at the inlet of said first reactor, more preferentially between 3 and 15 bara while being less than that at the inlet of said first reactor.

Preferably, stage ii) of the present process is carried out with a contact time between 1 and 100 s, preferably between 2 and 75 s, in particular between 3 and 50 s. Preferably, the HF/chlorinated compound molar ratio can vary between 1:1 and 150:1, preferably between 2:1 and 125:1, more preferentially between 3:1 and 100:1. An oxidant, such as oxygen or chlorine, can be added during stage ii). The molar ratio of the oxidant to the hydrocarbon compound can be between 0.005 and 2, preferably between 0.01 and 1.5. The oxidant can be pure oxygen, air, or a mixture of oxygen and nitrogen.

According to a preferred embodiment, stage i) is carried out at a temperature of between 310° C. and 420° C., advantageously between 310° C. and 400° C., preferably between 310° C. and 375° C., more preferentially between 310° C. and 360° C., in particular between 330° C. and 360° C.

According to a preferred embodiment, stage ii) is carried out at a temperature of between 320° C. and 440° C., advantageously between 320° C. and 420° C., preferably between 330° C. and 400° C., more preferentially between 330° C. and 390° C., in particular between 340° C. and 380° C.

Stage i) can be carried out at a temperature different from or equal to that of stage ii). When stage i) is carried out at a temperature different from that of stage ii), stage i) can be carried out at a temperature lower than that of stage ii) or at temperature greater than that of stage ii).

According to a preferred embodiment, the difference between the temperature at which stage i) is carried out and the temperature at which stage ii) is carried out is greater than 0.2° C., advantageously greater than 0.5° C., preferably greater than 1° C., more preferentially greater than 5° C., in particular greater than 10° C.; and less than 60° C., advantageously less than 55° C., preferably less than 50° C., more preferentially less than 45° C., in particular less than 40° C., more particularly less than 35° C., favorably less than 30° C., preferentially favorably less than 25° C., particularly favorably less than 20° C.

According to a preferred embodiment, said stream A and said at least one chlorinated compound are brought into contact prior to the entry of these into said second reactor. The resulting mixture is the mixture C.

Preferably, said at least one chlorinated compound is in the liquid state. The latter is vaporized by mixing with said stream A. The resulting mixture C is then in the gaseous form. In particular, the mixing between said stream A and said at least one chlorinated compound is carried out in a static mixer. Preferably, said at least one chlorinated compound is introduced into the static mixer via one or more spray nozzles. Said at least one chlorinated compound is thus sprayed in the form of droplets before being vaporized by mixing with said stream A, thus forming a mixture C in the gaseous form. The spraying of said at least one chlorinated compound in the form of fine droplets makes it possible to ensure a more efficient vaporization of this compound. For example, the mean diameter of the droplets thus produced can be less than 500 µm.

Preferably, bringing said stream A into contact with said at least one chlorinated compound in a static mixer generates a pressure drop from 100 mbar to 500 mbar, advantageously from 200 to 300 mbar. Thus, the pressure difference between the pressure at the inlet of said first reactor and the pressure at the inlet of said second reactor is from 100 mbar to 3.5 bar, advantageously from 150 mbar to 3.0 bar, preferably from 300 mbar to 2.5 bar, more preferentially from 450 mbar to 2.0 bar, in particular from 750 mbar to 1.75 bar, more particularly from 1 to 1.5 bar, 100 mbar to 500 mbar of which results from the use of said static mixer, advantageously 200 to 300 mbar of which results from the use of said static mixer.

Said mixture C can optionally be heated or cooled before it is introduced into said second reactor. This stage can be carried out via a heat exchanger in order to control the temperature at the inlet of said second reactor. Thus, when the mixture C is heated or cooled via a heat exchanger, a pressure drop of 300 to 700 mbar can be generated, advantageously of 400 to 600 mbar. In this case, the pressure difference between the pressure at the inlet of said first reactor and the pressure at the inlet of said second reactor is from 300 mbar to 2.5 bar, more preferentially from 400 mbar to 2.0 bar, in particular from 750 mbar to 1.75 bar, more particularly from 1 to 1.5 bar, 300 to 700 mbar of which results from the use of said heat exchanger to heat or cool said mixture C, advantageously 400 to 600 mbar of which results from the use of said heat exchanger to heat or cool said mixture C.

More particularly, if the mixing between said stream A and said at least one chlorinated compound is carried out in a static mixer and if the resulting mixture C is heated or cooled via a heat exchanger, as described in detail above, from 400 mbar to 1.2 bar can be generated, advantageously from 500 mbar to 1.0 bar. In this case, the pressure difference between the pressure at the inlet of said first reactor and the pressure at the inlet of said second reactor is from 400 mbar to 2.0 bar, in particular from 750 mbar to 1.75 bar, more particularly from 1 to 1.5 bar, 400 mbar to 1.2 bar of which results from the use of said static mixer and of said heat exchanger, advantageously 500 mbar to 1.0 bar of which results from the use of said static mixer and of said heat exchanger.

According to a preferred embodiment, the stream B is purified, preferably by distillation, in order to form a first stream comprising 2,3,3,3-tetrafluoropropene, HCl and 1,1,1,2,2-pentafluoropropane and a second stream comprising HF and 2-chloro-3,3,3-trifluoropropene. Said second stream can also comprise 1,2-dichloro-3,3,3-trifluoropropene.

Preferably, said stream B is distilled under conditions sufficient to form said first stream comprising 2,3,3,3-tetrafluoropropene, HCl and 1,1,1,2,2-pentafluoropropane, and said second stream comprising HF and 2-chloro-3,3,3-trifluoropropene and possibly 1,2-dichloro-3,3,3-trifluoropropene. In particular, the distillation can be carried out at a pressure from 2 to 6 bara, more particularly at a pressure from 3 to 5 bara. In particular, the temperature at the distillation column top is from −35° C. to 10° C., preferably from −20° C. to 0° C.

According to a preferred embodiment, said second stream is recycled in stage i). Said second stream can optionally be purified, in particular by distillation, before being recycled in stage i). The purification of said second stream can optionally be carried out in order to remove the 1,2-dichloro-3,3,3-trifluoropropene possibly present in it.

According to a preferred embodiment, said stream B obtained in stage ii) is cooled prior to the abovementioned purification. In particular, said stream B obtained in stage ii) is cooled to a temperature of less than 100° C., then distilled in order to form said first stream comprising 2,3,3,3-tetrafluoropropene, HCl and 1,1,1,2,2-pentafluoropropane, and said second stream comprising HF and 2-chloro-3,3,3-trifluoropropene and possibly 1,2-dichloro-3,3,3-trifluoropropene; the temperature at the distillation column top is from −35° C. to 10° C. and the distillation is carried out at a pressure from 2 to 6 bara; said second stream obtained at the distillation column bottom is recycled in stage i).

Said stream B can be cooled, before distillation, to a temperature of less than 95° C., advantageously of less than 90° C., preferably of less than 85° C., more preferentially of less than 80° C., in particular of less than 70° C., more particularly of less than 60° C., favorably of less than 55° C., advantageously favorably of less than 50° C., preferentially favorably of less than 40° C., more preferentially favorably of less than 30° C., particularly favorably of less than 25° C., more particularly favorably of less than 20° C. The cooling of the flow of products obtained at such temperatures facilitates the subsequent distillation of stage c).

The cooling of said stream B can be carried out by virtue of one or a plurality of heat exchangers. The cooling of said stream B can be carried out by passing the latter through one, two, three, four, five, six, seven, eight, nine or ten heat exchangers; preferably, the number of heat exchangers is of between 2 and 8, in particular between 3 and 7.

Preferably, the method according to the present invention is carried out continuously.

Example

The fluorination of HCFO-1233xf (2-chloro-3,3,3-trifluoropropene) to give HFO-1234yf (2,3,3,3-tetrafluoropropene) and optionally to give HFC-245cb (1,1,1,2,2-pentafluoropropane) is carried out in a first multitubular reactor. The stream of products which results from this fluorination feeds a second reactor. Said second reactor is also fed with a flow of hydrofluoric acid and of 1,1,1,2,3-pentachloropropane (HCC-240db). The fluorination of HCC-240db to give HCFO-1233xf (2-chloro-3,3,3-trifluoropropene) is carried out in the second multitubular reactor. A recycling loop, the flow rate of which is controlled, makes it possible to return certain products to the first reactor. The first and the second reactor contain a bulk catalyst based on chromium oxide. The catalyst is activated by a series of stages comprising drying, fluorination, treatment under air and fluorination with recycling. This multistage treatment makes it possible to render the catalytic solid active and selective.

In the first reactor, the fluorination process is carried out according to the following operating conditions:
an absolute pressure in the fluorination reactor of 6.1 bar absolute
a molar ratio of the HF to the sum of the organic materials fed by the recycling loop of between 15 and 20
a contact time of between 18 and 20 seconds
a constant temperature in the reactor of 350° C.

In the second reactor, the fluorination process is carried out according to the following operating conditions:
an absolute pressure in the fluorination reactor of 5.5 bar absolute
a molar ratio of the HF to the sum of the organic materials fed by the recycling loop of between 12 and 15
a contact time of between 11 and 13 seconds
a constant temperature in the reactor of 350° C.

The pressure difference between the pressure at the inlet of said first reactor and the pressure at the inlet of said second reactor is of 600 mbar. The flow rate of the recycling loop at the inlet of the first reactor varies from 34 to 38 kg/h. The flow rate for introduction of the 1,1,1,2,3-pentachloropropane into the second reactor varies from 3 to 7 kg/h. The contents of 1,1,1,2,2-pentafluoropropane (HFC-245cb) and of 1,2-dichloro-3,3,3-trifluoropropene (HFCO-1223xd) in the stream exiting from the $2^{nd}$ reactor are taken up in table 1 below.

TABLE 1

| Time (h) | Content of HFC-245cb at the outlet of the $2^{nd}$ reactor (% weight)* | Content of HCFO-1223xd at the outlet of the $2^{nd}$ reactor (% weight)* |
| --- | --- | --- |
| 185 h | 29.4 | 4.2 |
| 280 h | 30.6 | 5.0 |
| 440 h | 30.7 | 4.8 |
| 550 h | 27.7 | 4.9 |

*The contents are calculated on the basis of the total weight of the organic compounds in the stream exiting from the $2^{nd}$ reactor.

The applicant has observed that the contents of HFC-245cb and of HCFO-1223xd in the stream exiting from the second reactor decrease when the process is carried out with a pressure at the inlet of the first reactor which is greater than that at the inlet of the second reactor, compared with when the process is carried out at identical pressures in the two reactors.

The invention claimed is:

1. A process for the production of 2,3,3,3-tetrafluoropropene comprising the stages:
   i. in a first reactor, bringing 2-chloro-3,3,3-trifluoropropene into contact with hydrofluoric acid in the gas phase in the presence of a catalyst, in order to produce a stream A comprising 2,3,3,3-tetrafluoropropene, HF and unreacted 2-chloro-3,3,3-trifluoropropene; and
   ii. in a second reactor, bringing hydrofluoric acid into contact, in the gas phase in the presence or absence of a catalyst, with at least one chlorinated compound selected from the group consisting of 1,1,1,2,3-pentachloropropane, 2,3-dichloro-1,1,1-trifluoropropane, 2,3,3,3-tetrachloropropene and 1,1,2,3-tetrachloropropene, in order to produce a stream B comprising 2-chloro-3,3,3-trifluoropropene,
wherein the stream A obtained in stage i) feeds said second reactor used for stage ii); and the pressure at the inlet of said first reactor of stage i) is greater than the pressure at the inlet of said second reactor of stage ii).

2. The process as claimed in claim 1, wherein the pressure difference between the pressure at the inlet of said first reactor and the pressure at the inlet of said second reactor is from 100 mbar to 3.5 bar.

3. The process as claimed claim 1, wherein stage i) and stage ii) are carried out in the presence of a catalyst.

4. The process as claimed in claim 3, wherein the catalyst is based on chromium and also comprises a co-catalyst selected from the group consisting of Ni, Zn, Co, Mn and Mg.

5. The process as claimed in claim 1, wherein the stream B also comprises 2,3,3,3-tetrafluoropropene, HF, HCl and 1,1,1,2,2-pentafluoropropane.

6. The process as claimed in claim 1, wherein the stream B is purified in order to form a first stream comprising 2,3,3,3-tetrafluoropropene, HCl and 1,1,1,2,2-pentafluoropropane and a second stream comprising HF and 2-chloro-3,3,3-trifluoropropene.

7. The process as claimed in claim 6, wherein said second stream is recycled in stage i).

8. The process as claimed in claim 1, wherein said stream A and said at least one chlorinated compound are brought into contact prior to the entry of these into said second reactor.

9. The process as claimed in claim 1, wherein the temperature at which stage i) is carried out is different from that at which stage ii) is carried out; and the difference between the temperature at which stage i) is carried out and the temperature at which stage ii) is carried out is greater than 0.2° C. and less than 60° C.

10. The process as claimed in claim 1, wherein the stream B is cooled to a temperature of less than 100° C., then distilled in order to form a first stream comprising 2,3,3,3-tetrafluoropropene, HCl and 1,1,1,2,2-pentafluoropropane, and a second stream comprising HF and 2-chloro-3,3,3-trifluoropropene and possibly 1,2-dichloro-3,3,3-trifluoropropene; the temperature at the distillation column top is from −35° C. to 10° C. and the distillation is carried out at a pressure from 2 to 6 bara; said second stream obtained at the distillation column bottom is recycled in stage i).

11. The process as claimed in claim 3, wherein the catalyst is a chromium-based catalyst comprising a chromium oxyfluoride, a chromium oxide, a chromium fluoride or a mixture of these.

* * * * *